United States Patent
Déverin et al.

(10) Patent No.: US 6,914,721 B2
(45) Date of Patent: Jul. 5, 2005

(54) PRISM CONSTRUCTION FOR SIMULTANEOUS ZERO-DEGREE AND OBLIQUE ILLUMINATION OF A STEREOSCOPIC SURGICAL MICROSCOPE

(75) Inventors: Jacques Alain Déverin, Widnau (CH); Ulrich Sander, Rebstein (CH)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 39 days.

(21) Appl. No.: 10/229,411

(22) Filed: Aug. 28, 2002

(65) Prior Publication Data

US 2003/0048528 A1 Mar. 13, 2003

(30) Foreign Application Priority Data

Sep. 7, 2001 (DE) .......................... 101 44 067

(51) Int. Cl.⁷ .......................... G02B 21/06; G02B 21/00
(52) U.S. Cl. ..................... 359/388; 359/368; 359/385
(58) Field of Search ............................... 359/368–390, 359/431, 831–837; 351/200–247

(56) References Cited

U.S. PATENT DOCUMENTS

| | | | | |
|---|---|---|---|---|
| 4,674,845 A | * | 6/1987 | Matsumura | 359/377 |
| 4,715,704 A | | 12/1987 | Biber et al. | 351/207 |
| 5,155,509 A | * | 10/1992 | Kleinberg | 351/205 |
| 5,288,987 A | * | 2/1994 | Vry et al. | 250/201.3 |
| 5,627,613 A | * | 5/1997 | Kaneko | 351/221 |
| 5,898,518 A | * | 4/1999 | Biber | 359/385 |
| 6,624,932 B2 | * | 9/2003 | Koetke | 359/389 |

FOREIGN PATENT DOCUMENTS

| | | | |
|---|---|---|---|
| DE | 40 28 605 A1 | 3/1992 | |
| DE | 196 50 773 A1 | 7/1997 | |
| DE | 195 38 382 A1 | 4/1998 | |
| DE | 101 08 254 A1 | 8/2002 | |
| EP | 1 153 569 A2 | 11/2001 | |
| JP | 09-105866 | 4/1997 | |
| JP | 10-133122 | * 5/1998 | 359/385 |
| WO | WO 99/59016 | 11/1999 | |

OTHER PUBLICATIONS

Carl Zeiss Brochure for the OMPI MDO.—Zeiss, Germany—Oct. 1991, pp 1–4.

* cited by examiner

Primary Examiner—Thong Q Nguyen
(74) Attorney, Agent, or Firm—Hodgson Russ LLP

(57) ABSTRACT

The invention concerns an apparatus for simultaneous zero-degree and oblique illumination for an optical viewing device, in particular a stereoscopic surgical microscope, which contains a shiftable prism combination (3) for deflecting a first illumination sub-beam a long distance from the optical axis (12) of the main objective in order to obtain an oblique illumination beam (9) (oblique illumination), and for deflecting a second illumination sub-beam (8) a short distance from the optical axis (12) of the main objective in order to obtain a zero-degree illumination (8).

9 Claims, 3 Drawing Sheets

PRISM CONSTRUCTION FOR SIMULTANEOUS ZERO-DEGREE AND OBLIQUE ILLUMINATION OF A STEREOSCOPIC SURGICAL MICROSCOPE

CROSS REFERENCE TO RELATED APPLICATIONS

This application claims priority of the German patent application 101 44 067.7 filed Sep. 7, 2001 which is incorporated by reference herein.

FIELD OF THE INVENTION

The invention concerns a prism construction for simultaneous zero-degree and oblique illumination of a stereoscopic surgical microscope.

BACKGROUND OF THE INVENTION

Stereoscopic surgical microscopes often possess a system for reflecting in illumination with which an illumination beam path is split by way of a deflection device into an oblique and a zero-degree partial beam, which are switched into the main beam path of the microscope.

Reflected-in beam paths for illumination of a specimen field are used in a wide variety of applications, in particular including ophthalmology. In this context, the patient's eye is usually illuminated directly by the surgical microscope's illumination. If the brightness is excessive, this greatly endangers the retina in particular but also the cornea.

Repeated attempts have therefore been made to exclude or minimize this hazard. For that purpose, for example in U.S. Pat. No. 4,715,704 of Zeiss, an opaque stop whose location is conjugated with the specimen plane was pivoted into the illumination beam path. A stop having a physical and spectral gradient is described in DE-A-101 08 254. These stops all result in a darkening of the specimen field, which of course provides the best eye protection. As a result, however, the surgeon's work is also impeded by a limited view. What is actually desirable is therefore a certain amount of eye protection and sufficient illumination for the surgeon.

One solution consists in an ophthalmological objective of Leica, in which the zero-degree illumination can be swung out by rotating the objective (as of mid-1980).

Olympus proposes shutting off the zero-degree illumination using a shutter (see Japanese Patent publication number 09105866). With both solutions, the harmful zero-degree illumination is shut off, but the specimen field continues to be illuminated by the so-called 6-degree component. The Applicant's Swiss patent application number CH-977/00 makes a proposal in which, by pivoting out various lens elements, the image of the harmful light on the retina is modified in such a way that the harmfulness is considerably reduced.

Olympus proposes shutting off the zero-degree illumination using a shutter (09105866). With both solutions, the harmful zero-degree illumination is shut off, but the specimen field continues to be illuminated by the so-called 6-degree component. The Applicant's Swiss patent application CH-977/00 makes a proposal in which, by pivoting out various lens elements, the image of the harmful light on the retina is modified in such a way that the harmfulness is considerably reduced.

A further device, but one that is complex in terms of optical configuration, is evident from the Carl Zeiss brochure for the OPMI MD®. Here the patient's eye can be illuminated with a built-in oblique illumination system when the red reflection is no longer needed.

Carl Zeiss (in DE-A-402 86 05) and Möller (in DEA-196 50 773) describe an assemblage having two deflection means, in which the first is arranged either partially or entirely shiftably. The further deflection means are arranged close to the observation beam paths, entirely or partially surrounding them. A uniform red reflection is thereby obtained.

In 1998 the Applicant proposed (in WO/A-99/59016) an illumination apparatus in which one oblique light flux and one parallel to the microscope's main axis are created, and can be regulated independently of one another. The disadvantages of this solution are: with a zero-degree prism snorkel, only a portion of the illumination pupil is used; this can result in vignetting and field cutoff. In addition, the zero-degree illumination field is smaller than the 6-degree field. The result of this is that in some circumstances, the red reflection does not occur everywhere in the illuminated field. This arrangement also causes at least three reflections to be imaged on the cornea, which in some circumstances can be undesirable.

SUMMARY OF THE INVENTION

The objects of the invention are thus to create an illumination apparatus which optimally utilizes the light inlet pupil and, when the red-reflection illumination of the ocular fundus is no longer needed, makes possible effective eye protection for the patient without reducing the intensity of the specimen field illumination, thus eliminating the disadvantages of the existing art mentioned initially. The sequence of the two objects can also be reversed, namely that an effective eye protection is made possible, and moreover the light inlet pupil is optimally utilized.

This object is achieved by way of the following actions:

The deflection element is embodied as a prism combination for deflecting a first illumination sub-beam a long distance from the optical axis of the main objective (oblique illumination) and for deflecting a second illumination sub-beam a short distance from the optical axis of the main objective (implementation of zero-degree illumination). The deflection element accepts light from the entire illumination pupil, and thus covers the entire area of the first deflection element (6 degrees). A very low overall height is also thereby obtained.

Protection for the patient's eye is provided by the fact that the prism combination with the downstream illuminating optical system is shifted away from the observation beam paths. The result of this is that the light spot which occurs on the retina, and can be harmful in the vicinity of the macula, is also moved away from that location. The surgeon shifts the entire illumination unit when he or she no longer needs the red reflection; the same specimen field illumination is then nevertheless still available, but now without the red reflection, and merely at a different angle. This shift can be actuated, according to the present invention, in manual or motorized fashion. The eye protection can, of course, also be combined with a different construction for reflecting in light (omitting the prism combination), and conversely the prism combination according to the present invention can also advantageously be used independently of the shifting capability.

The zero-degree snorkel is replaced by the fact that the zero-degree light is no longer reflected in directly between the observation beam paths, but instead is shifted slightly in the direction of the light source. For this purpose, according to a particular embodiment of the invention, a new shape is selected for the zero-degree deflection element.

BRIEF DESCRIPTION OF THE DRAWINGS

The invention will be explained in more detail, by way of example, with reference to schematic depictions.

In the Figures.

The Figures are described in interconnected and overlapping fashion. Identical reference characters denote identical components; reference characters with different indices indicate functionally identical components.

DETAILED DESCRIPTION OF THE INVENTION

Figure 1:
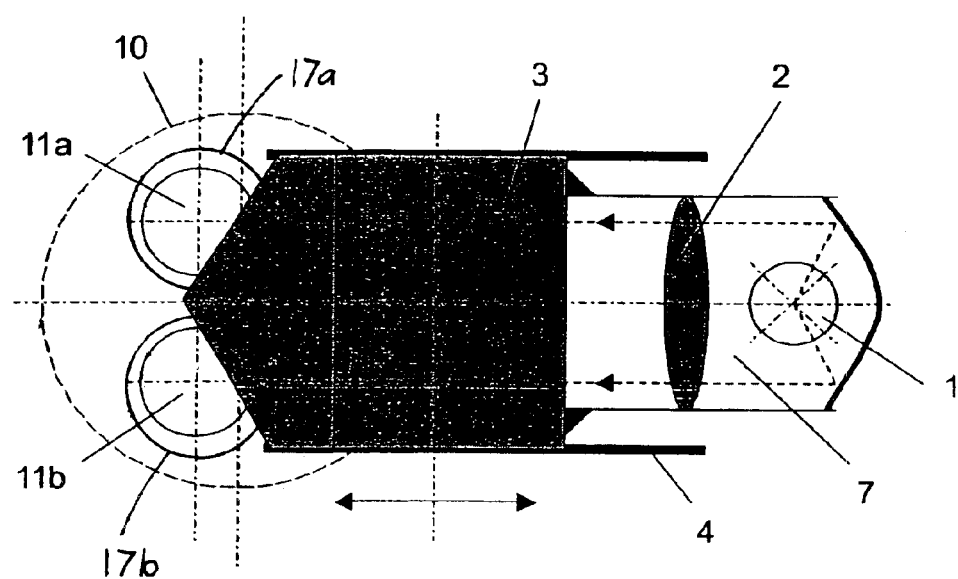
FIG. 1 schematically depicts, in plan view, a system for reflecting illumination into a microscope's main beam path via a prism combination.

FIG. 1 schematically depicts, in plan view, a system for reflecting in illumination having a light source 1, an illuminating optical system 2, a prism combination 3 immovably joined to light source 1 and illuminating optical system 2, and having a shifting apparatus 4 for prism combination 3, an illumination beam 7, a main objective 10, observation beam paths 11a, 11b, and lens tubes 17a, 17b respectively associated with observation beam paths 11a, 11b.

Figure 2:
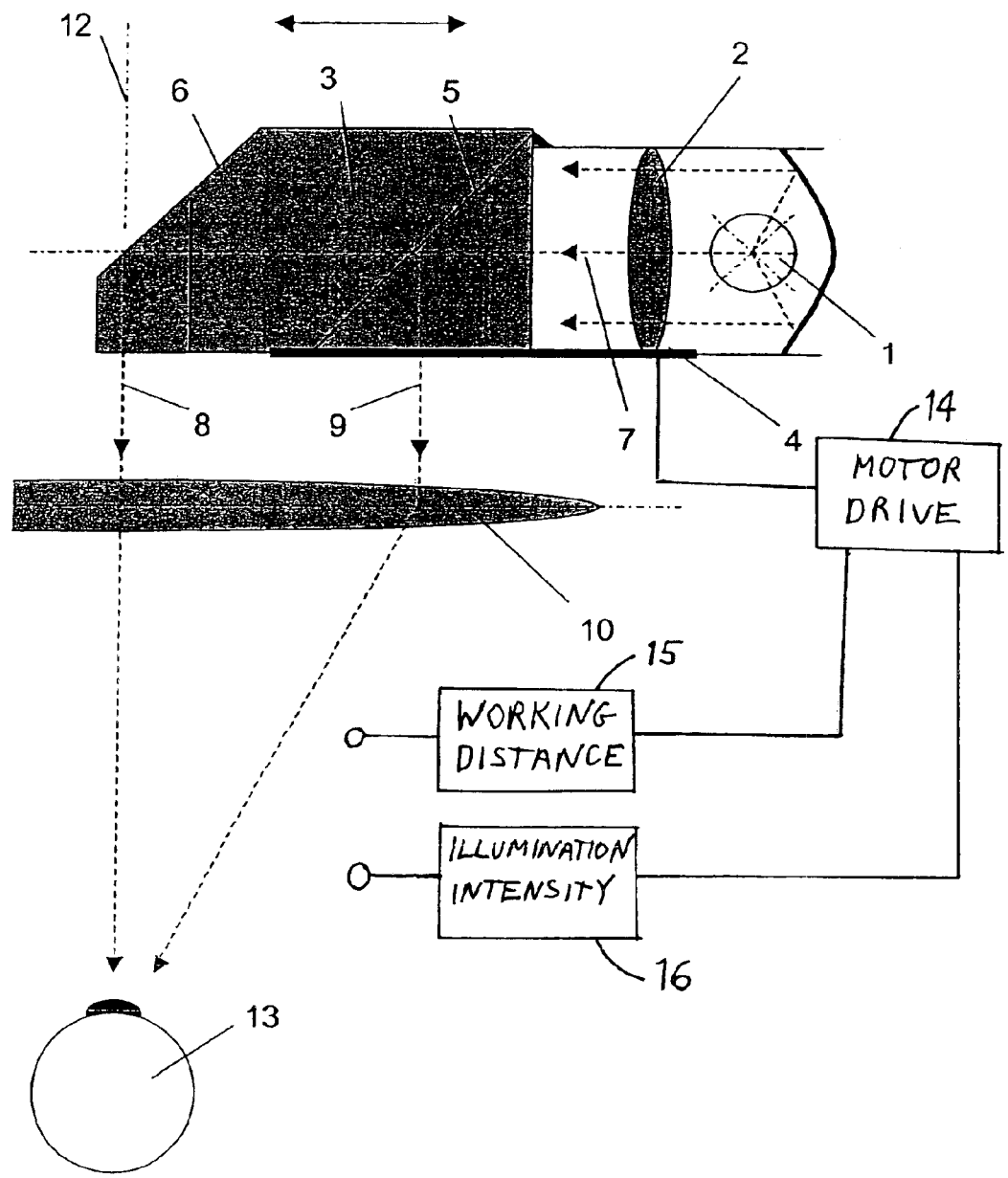
FIG. 2 schematically depicts a system for reflecting illumination into a microscope's main beam path by means of a prism combination that is in the centered state.

FIG. 2 schematically shows the system for reflecting in illumination depicted in FIG. 1, as a sectioned image seen from the side, having: a light source 1; an illuminating optical system 2; a prism combination 3, with a beam splitter surface 5 and a totally reflective mirror surface 6, that is located centeredly with respect to optical axis 12 of the main objective; an illumination sub-beam 8 for zero-degree illumination of specimen 13; an illumination sub-beam 9 that deviates from optical axis 12 of the main objective; and a main objective 10. Lens tubes 17a, 17b residing above prism combination 3 are not shown. As can be seen in FIG. 2, illumination beam 7 travels within prism combination 3 in a direction perpendicular to optical axis 12, and surfaces 5 and 6 are each at an angle of approximately 45° to the optical axis 12.

Figure 2A:
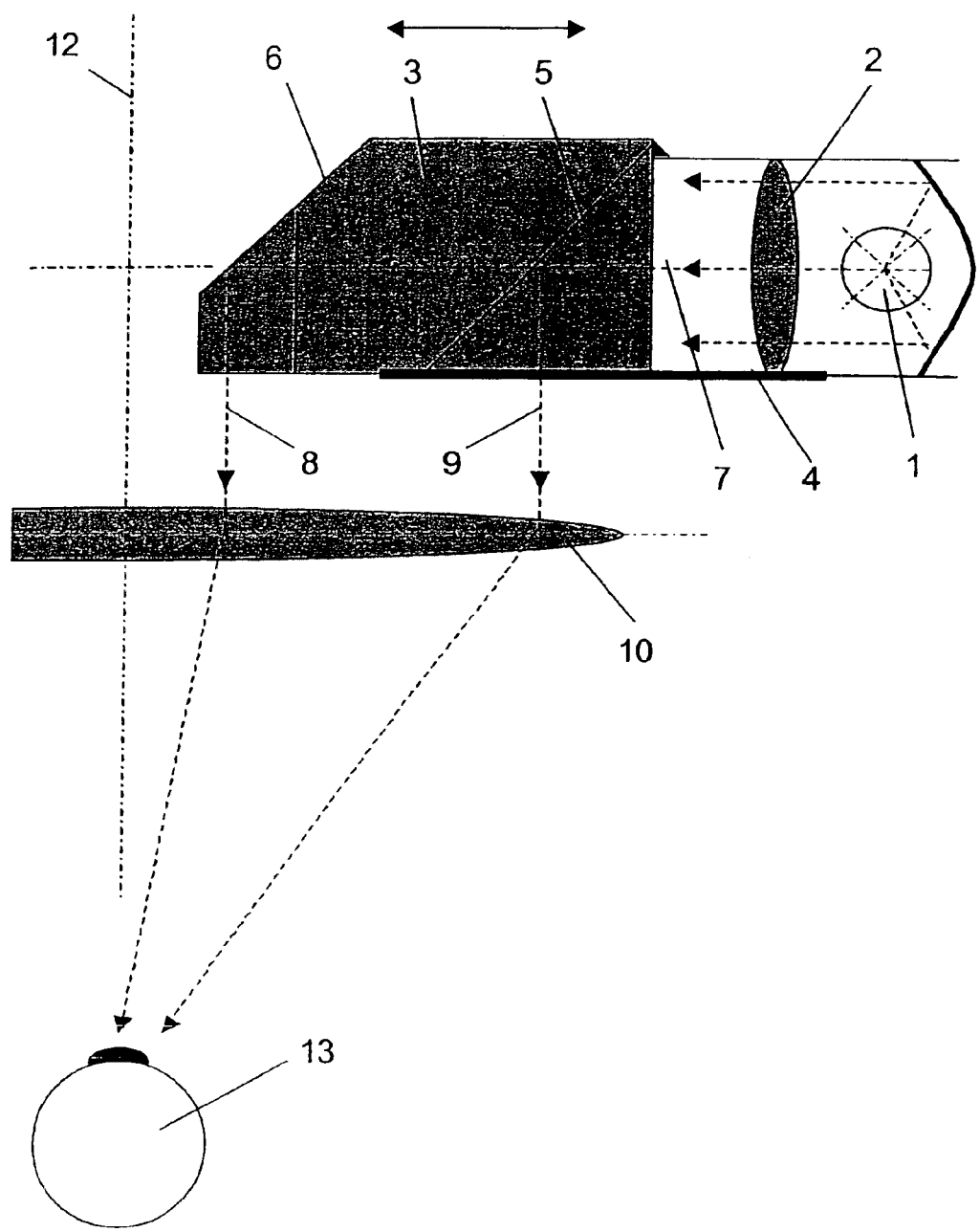
FIG. 2a is a depiction similar to FIG. 2, the prism combination being in the state shifted radially with respect to the optical axis.

FIG. 2a, similarly to FIG. 2, schematically shows illumination sub-beams 8, 9 when prism combination 3 is in the radially shifted state with respect to optical axis 12 of the main objective.

Referring again to FIG. 2, possible advantageous enhancements of the basic invention are illustrated in schematic fashion. Shifting apparatus 4 can be driven by a motorized drive system 14 which in turn can be connected to a distance measurement system 15 for measuring the distance between main objective 10 and a patient's eye 13 that is being observed, such that when a distance to the patient's eye is too short, the prism combination 3 is moved out of said centered state. As an alternative or in addition to this first safeguard, a second safeguard is possible wherein motorized drive system 14 is connected to a light-intensity measurement system 16 for detecting the intensity of illuminating light at a location in the optical system, such that when a luminance is too high, the prism combination 3 is moved out of the centered state.

Manner of Operation (FIG. 2)

When a prism combination 3 according to the present invention having a beam splitter surface 5 and a mirror surface 6 is used in the centered state, illumination beam 7 is deflected into two illumination sub-beams 8, 9 coaxial with optical axis 12 of the main objective. This means that beam splitter surface 5 brings about, via main objective 10, an illumination of specimen 13 that deviates from optical axis 12 of the main objective. Mirror surface 6 images the remainder of illumination beam 7 into optical axis 12 of the main objective, and illuminates specimen 13 at an angle of approximately zero degrees (zero-degree illumination).

(FIG. 2a)

If prism combination 3 is then shifted, together with illuminating optical system 2 and light source 1 joined rigidly to it, radially outward with respect to optical axis 12 of the main objective, an oblique illumination of specimen 13 that deviates from optical axis 12 of the main objective is achieved for both of the illumination sub-beams 8, 9 that are generated. The red reflection, and thus intensive illumination of the ocular fundus in the vicinity of the macula, can thereby be avoided. The prism combination 3 is movable through a continuous range of radial positions relative to optical axis 12 so that any illumination angle within a continuous range of illumination angles is selectable.

As a variant, an assemblage can also be selected in which only prism combination 3, but not illuminating optical system 2 and/or lamp 1, is shifted.

The illumination situation for microscopes is improved by the invention:

Because the illumination beam path is, according to the present invention, reflected in via a deflection element (which is preferably shiftable with respect to the optical axis of the microscope) that generates two optical beam paths, it is possible (as known per se) to generate simultaneously a zero-degree and an oblique illumination of the specimen (cf. applicant's patent application WO 99/59016)

Shifting of the deflection element radially outward, individually or together with the illumination system, converts the zero-degree illumination into an oblique illumination, thereby preventing the red reflection. The shiftability according to the present invention is independent of the nature of the reflecting in assemblage. For example, an assemblage could be embodied in accordance with the applicant's aforementioned International Application WO 99/59016, with the difference that the deflection element is shiftable perpendicular to the optical axis of the main objective.

Vignetting and field cutoff of the illuminated to field are prevented.

The two illuminated fields are identical in size and homogeneously illuminated.

In the centered state, the red reflection is visible over the entire illuminated field.

A maximum of two cornea reflections, located in very close proximity to one another, are created.

In accordance with the particular embodiment, the new zero-degree prism according to the present invention is located, in its proposed form, very close to the two stereoscopic observation beam paths, so that in particular a good red reflection can be produced.

One particular development is constituted by the combination of the invention with DE-A-195 38 382, which describes a system in which, by way of an automatic distance measuring system, warning signals are issued or the illumination is reduced or shut off if the distance falls below a critical value. This device can be used to automatically shift the illumination prism, with or without the illuminating optical system and lamp, away from the observation pupil when critical conditions exist.

Although the text above refers to a surgical microscope, the invention is nevertheless not limited thereto, but rather is also available to other users of optical devices having additional illumination systems (microscopes in circuit-board use, etc.) The claims are to be construed correspondingly broadly.

The Parts List and FIGS. 1, 2, and 2a are, together with the subject matter described and protected in the claims, integral constituents of the disclosure of this Application.

PARTS LIST

1 Light source
2 Illuminating optical system
3 Prism combination
4 Shifting apparatus
5 Beam splitter surface for oblique illumination
6 Mirror surface for zero-degree illumination
7 Illumination beam
8 Illumination sub-beam for zero-degree illumination
9 Illumination sub-beam for oblique illumination
10 Main objective
11 Observation beam path a, b
12 Optical axis of main objective
13 Specimen
14 Motorized drive
15 Distance measurement system
16 Light-intensity measurement system
17 Lens tube a, b

What is claimed is:

1. An optical system for use in combination with a stereoscopic microscope of a type including a main objective (10) having an optical axis (12) and two stereoscopic observation beam paths (11a, 11b) each having a respective lens tube associated therewith, said optical system being used for simultaneous zero-degree and oblique illumination of an observed specimen (13), said optical system comprising:

an illumination beam (7); and
a prism combination (3) arranged between said main objective (10) and said lens tubes (17) to receive said illumination beam, said prism combination splitting said illumination beam into a first illumination sub-beam (9) and a second illumination sub-beam (8) and deflecting said first and second sub-beams to said main objective, said first illumination sub-beam being deflected along a path spaced relatively far from said optical axis to obtain said oblique illumination and said second illumination sub-beam being deflected along a path relatively close to said optical axis to obtain said zero-degree illumination;
wherein a portion of said prism combination (3) directed toward said two stereoscopic observation beam paths tapers symmetrically toward said optical axis (12) of said main objective (10) in order to achieve optimum and vignetting-free observation, and wherein said prism combination (3) is radially movable relative to said optical axis (12) of said main objective (10).

2. The optical system as defined in claim 1, wherein said prism combination (3) is centerable relative to said optical axis (12) of said main objective (10) such that when said prism combination (3) is in a centered state, said zero-degree illumination of said specimen (13) is obtained using said second illumination sub-beam (8) and said oblique illumination of said specimen (13) is obtained using said first illumination sub-beam (9).

3. The optical system as defined in claim 2, wherein said prism combination (3) can be decentered relative to said optical axis (12) of said main objective (10) such that when said prism combination (3) is in a decentered state, an oblique illumination is obtained using both said first and second illumination sub-beams (9, 8).

4. The apparatus as defined in claim 3, wherein said prism combination (3) is movable radially relative to said optical axis (12) of said main objective (10) in manual or motorized fashion.

5. The apparatus as defined in claim 4, further comprising a motorized drive system (14) for moving said prism combination (3) radially relative to said optical axis (12) of said main objective (10).

6. The apparatus as defined in claim 5, wherein said motorized drive system (14) is coupled to a distance measurement system (15) which, in an operating state and when a distance to the patient's eye is too short, moves said prism combination (3) out of said centered state.

7. The apparatus as defined in claim 5, wherein said motorized drive system (14) is coupled to a light-intensity measurement system (16) which, in an operating state and when a luminance is too high, shifts said prism combination (3) out of said centered state.

8. The optical system as defined in claim 1, wherein said prism combination (3) is movable through a continuous range of radial positions relative to said optical axis (12) of said main objective (10), whereby any illumination angle within a continuous range of illumination angles is selectable.

9. An optical system for use in combination with a stereoscopic microscope of a type including a main objective (10) having an optical axis (12) and two stereoscopic observation beam paths (11a, 11b) each having a respective lens tube associated therewith, said optical system being used for simultaneous zero-degree and oblique illumination of an observed specimen (13), said optical system comprising:

a light source (1) and an illuminating optical system (2) for providing an illumination beam (7); and
a prism combination (3) arranged between said main objective (10) and said lens tubes (17) to receive said illumination beam, said prism combination splitting said illumination beam into a first illumination sub-beam (9) and a second illumination sub-beam (8) and deflecting said first and second sub-beams to said main objective, said first illumination sub-beam being deflected along a path spaced relatively far from said optical axis to obtain said oblique illumination and said second illumination sub-beam being deflected alone a path relatively close to said optical axis to obtain said zero-degree illumination;
wherein a portion of said prism combination (3) directed toward said two stereoscopic observation beam paths tapers symmetrically toward said optical axis (12) of said main objective (10) in order to achieve optimum and vignetting-free observation, and wherein said prism combination (3) is radially movable relative to said optical axis (12) of said main objective (10) together with said illuminating optical system (2) and said light source (1).

* * * * *